United States Patent [19]

Strahwald et al.

[11] 4,354,509
[45] Oct. 19, 1982

[54] APPARATUS FOR APPLICATION OF AN ELECTRODE SYSTEM ON A PATIENT'S BODY

[75] Inventors: Franz Strahwald, Ebermannstadt; Erich Szehi, Buckenhof, both of Fed. Rep. of Germany

[73] Assignee: Siemens Aktiengesellschaft, Berlin and Munich, Fed. Rep. of Germany

[21] Appl. No.: 203,799

[22] Filed: Nov. 3, 1980

[30] Foreign Application Priority Data

Nov. 20, 1979 [DE] Fed. Rep. of Germany ... 7932816[U]

[51] Int. Cl.³ .............................................. A61N 1/04
[52] U.S. Cl. ..................................... 128/803; 128/639
[58] Field of Search .............................. 128/639–641, 128/644, 207.21, 783, 798, 802, 803

[56] References Cited

U.S. PATENT DOCUMENTS

| | | | |
|---|---|---|---|
| 2,784,715 | 3/1957 | Kestler | 128/207.21 |
| 3,556,105 | 1/1971 | Shepard | 128/798 |
| 4,023,574 | 5/1977 | Nemec | 128/420 A |
| 4,092,985 | 6/1978 | Kaufman | 128/798 X |

FOREIGN PATENT DOCUMENTS

| | | | |
|---|---|---|---|
| 1965195 | 7/1971 | Fed. Rep. of Germany | 128/640 |
| 2735050 | 2/1979 | Fed. Rep. of Germany | 128/640 |
| 498527 | 1/1939 | United Kingdom | 128/803 |

*Primary Examiner*—Lee S. Cohen
*Attorney, Agent, or Firm*—Hill, Van Santen, Steadman, Chiara & Simpson

[57] ABSTRACT

In an exemplary embodiment, for application of a multiple electrode for interference current therapy, the electrode system comprises a flexible formed part of electrically insulating plastic and individual electrode contact parts. The object of the disclosure is to simplify the application of an electrode system on the patient's body as far as possible. In accordance with the disclosure, the carrier for the contacting agent is a fleece material part whose external contour is slightly greater than the exterior perimeter of the formed part of the electrode system, the fleece material part having a covering of insulating material on its side not facing the application surface such that the electrode system is insertable between the fleece material part and the covering. The carrier for the contact agent thus likewise forms a flexible pocket for the electrode system.

7 Claims, 4 Drawing Figures

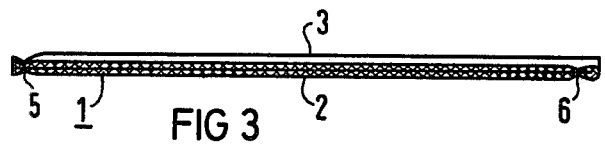
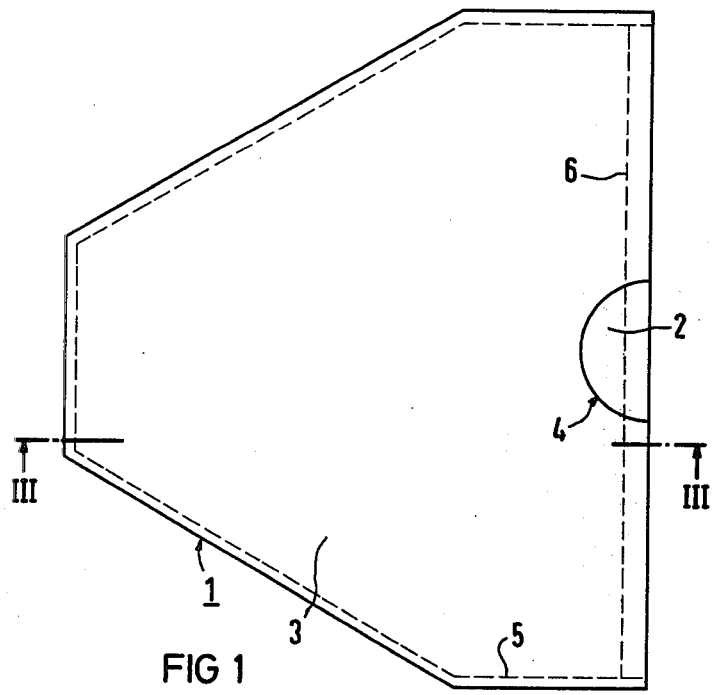
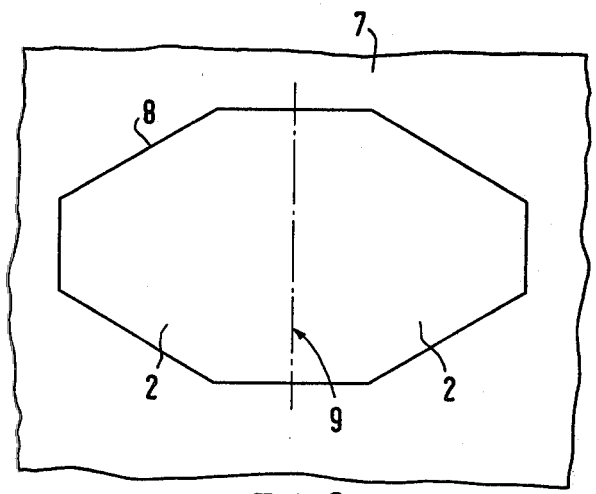

APPARATUS FOR APPLICATION OF AN ELECTRODE SYSTEM ON A PATIENT'S BODY

BACKGROUND OF THE INVENTION

The invention relates to an apparatus for application of an electrode system (or array) on a patient's body, in particular for application of a multiple electrode for interference current therapy which exhibits a flexible formed part comprised of electrically insulating plastic as the support of individual electrode contact parts, whereby a carrier for a contacting agent, such as liquid-absorbent paper, fleece material, or the like, can be placed between the contact part and the application location on the patient's body.

For an effective stimulation current therapy, additional contacting agents are necessary between the electrodes and the skin at the application location of the patient's body. Such contacting agents, in the simplest instance, can be sponge members capable of absorbing contact fluid which, due to their softness, cling (or adhere) well to the body part to be treated. Also thin absorbent papers, fleece materials, or the like, have proven suitable for this purpose, which merely need to moistened with water in order to establish the electrical contact. The design of such supports for contacting agents for the purpose of reducing the contact resistance: electrode-skin in the case of simple electrodes and multiple electrodes is, for example, specifically described in the U.S. patent application Ser. No. 930,062, now abandoned, in conjunction with electrode contact parts comprised of conductive foam plastics. In practice, however, for stimulation current therapy, the conventional electrode systems are presently being placed in inserts consisting of viscose-sponge, whereby the entire insert likewise serves as carrier for the contact fluid and as support-mounting for the electrodes. Such viscose-sponge pockets, however, have a series of disadvantages. On the one hand, the mechanical strength (or stability) of the sponge members as a whole is comparatively low, whereby there additionally results, due to the shrinkage upon drying, a poor accuracy as to size of the processed viscose-sponge. Upon drying such sponge members also become hard, as a consequence of which, in the dry state, the hard sponge body can easily break.

SUMMARY OF THE INVENTION

Accordingly, it is the object of the invention to disclose an apparatus for application of an electrode system on a patient's body which is soft and pliant for applying on the patient's body even in the dry state. The liquid-absorbent carrier for the contacting agent is not to vary in its accuracy as to size even in the case of longer use, particularly it is not to shrink. The evaporation of liquid into the environment is to be kept here as low as possible.

The object is solved in accordance with the invention in that the carrier for the contacting agent is a part of fleece material of a type whose exterior contour is slightly greater than the exterior perimeter of the formed part of the electrode system, the fleece material part having, on its side not facing the application surface, a covering consisting of insulating material such that the electrode system is capable of being inserted between the fleece material part and the covering.

The fleece material is preferably bound together with the covering except for an edge on the circumference. Thus, an electrode pocket is formed; simultaneously, through utilization of a sheet consisting of polyvinyl chloride, or the like, as covering, it is made possible that a drying of the fleece material is largely eliminated. The effects of temperature and humidity differences in the surrounding air are thus eliminated. Altogether the humidity is kept in the fleece also over longer periods of treatment and thus a good electric contacting is constantly guaranteed.

The fleece material is preferably manufactured in the form of an irregular fiber fleece material having a synthetic wool base with polyolefin fibers. Such fleece materials are presently on the market, for example, for the purpose of covering wounds and the like, under the name "VILEDON T 1557". They have been developed with good cutaneous tolerance specifically for medical applications. Already during manufacture irregular fiber fleece materials of this type have at least one completely smooth side. If one employs the irregular fiber materials which can be purchased on the market, a doubled contour (or profile) of the fleece material part can be punched out in corresponding symmetry, whereby, through folding together along the mirror symmetry plane, both exterior surfaces are then already provided with a completely smooth form. Subsequently, the covering consisting of plastic sheet is stitched on the circumference except for one edge.

The inventive application aids can be manufactured for any desired electrode systems in all sizes and/or forms. In particular for utilization in the case of so-called star electrodes, the surface area of these electrode pockets is designed approximately in the manner of an equilateral triangle with edges cut off at right angles. A star electrode can then, for example, be readily inserted in the pockets formed by means of stitching-on the transparent plastic sheets. It is particularly advantageous that, during application of the electrode system on the patient's body, the correct fit (or positioning) of said electrode system can be controlled due to the transparent covering.

Further advantages and details of the invention shall be apparent from the following Figure description of exemplary embodiments on the basis of the accompanying drawing sheets in conjunction with the remaining subclaims; and other objects, features and advantages will be apparent from this detailed disclosure and from the appended claims.

BRIEF DESCRIPTION OF THE DRAWINGS

FIG. 1 illustrates an inventive apparatus in plan view;

FIG. 2 illustrates a web of fabric with a doubled punched contour (or profile) for the purpose of manufacturing a fleece part having surfaces which are smooth on both sides;

FIG. 3 illustrates a section of FIG. 1 along the line III—III, wherein a punched part according to FIG. 2 is employed.

DETAILED DESCRIPTION

Figure 4:
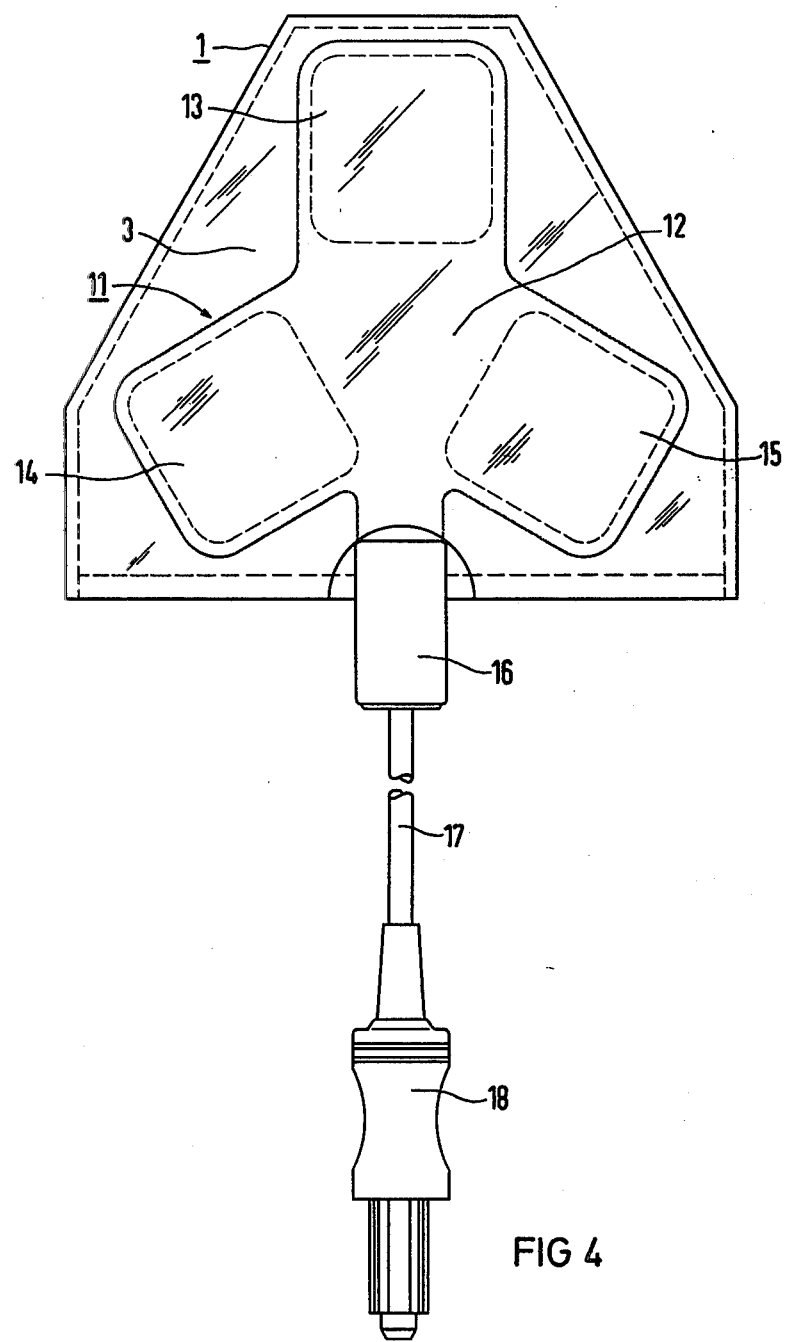
FIG. 4 illustrates the exemplary embodiment according to FIG. 1 with a star electrode inserted therein.

FIGS. 1, 3 and 4 are illustrated in the natural scale so as to show the actual size of an exemplary embodiment; FIG. 2, by contrast, is illustrated in a reduced scale. Identical parts are provided in the Figures with the same reference characters.

In FIGS. 1 and 3, 1 designates an electrode pocket. The latter consists of a surface area 2 consisting of irregular fiber fleece material, on which a sheet 3 of polyvinyl chloride or the like is securely stitched. Specifically for the purpose of accommodating a triple electrode, designed in the form of a so-called star electrode, the surface area 2 is designed to be triangular and at least isosceles, whereby the corners of this isosceles triangle are cut in such a fashion that symmetry prevails relative to the mean perpendicular to the base line. Altogether a hexagonal surface area results comprising two edges each which are parallel to one another in pairs. The two triangle (obliquely extending) edges can also be selectively designed to be concave. The cover sheet 3 exhibits a semicircular recess 4 in the direction of the base edge of the pocket 1.

As the fleece material, an irregular fiber fleece material having a synthetic wool base with polyolefin fibers is employed. A material of this type is known on the market under the name "VILEDON T 1557", specifically for medical applications, such as wound coverings, or the like. It is distinguished, in particular, by its good cutaneous tolerance and can also be utilized in a hygienically satisfactory manner over longer periods. In the dry state as well as in the moist state, this material is soft and pliant, so that it can be applied on randomly-shaped body parts; for the purpose of electric contact-making it is readily absorbent for an adequate liquid quantity.

Generally, the irregular fleece material found on the market already exhibits at least one completely smooth side. Since this material is relatively thin, it has proven expedient to punch out of the raw material web a part having a doubled surface area which is formed mirror-symmetrically relative to a center plane. The punched part is then merely folded along this symmetry plane, whereby expediently the exterior surfaces already form the completely smoothly formed surfaces. In FIG. 2 such a punched part 8 from a web of fabric 7 is illustrated.

After folding together, the correspondingly formed sheet is placed on the surface area according to FIG. 1 and is stitched on by means of a stitch seam 5. Merely the double part is connected along the seam 6. Thus, on this base line, the pocket formed by the fleece material part 2 and sheet 3 is open. An electrode system can here be readily inserted between the parts 2 and 3.

In FIG. 4, a triple electrode 11 designed in the form of a star electrode is inserted in an electrode pocket 1 according to FIG. 1. Such a star electrode exhibits a formed part 12 consisting of insulating plastic with three contact parts 13 through 15, offset by 120°, respectively, consisting of electrically conductive plastic. Due to the plastic parts which are interconnected through vulcanization, electrodes of this type are entirely smooth (or planar) at the application surface. They are flexible throughout, so that they can be randomly applied. The star electrode 11 has an electric connection 16 which can be connected, via an operating cable 17 and a plug and socket connector 18 with a (non-illustrated) stimulation current operating apparatus.

If an electrode arrangement is correctly inserted, as in FIG. 4, the connection 16 is seated in the semicircular recess 4 of the covering 3. Through utilization of a transparent sheet material as covering 3, the correct fit (or positioning) of the electrode system can be checked during application.

As previously stated, specifically irregular fiber fleece material is particularly well suited for the inventive apparatus on account of its softness and pliability. Due to the sheet covering on the side not facing the application surface, the evaporation of contact fluid into the environment during use is largely prevented and, in addition to the humidity insulation, an electric insulation is also guaranteed. Due to the skin humidity of the patient and the largely impervious covering relative to the environment, ideal contacting conditions result at the application location of the patient's body also over longer treatment times.

In the above exemplary embodiment of the invention, the electrode pocket consisting of fleece material and an insulating covering was specifically described for a star electrode. Also in the case of other electrode systems, for example, band electrodes, the size of the pocket is entirely correspondingly matched (or adapted) to the size and form of the respective electrode sets; namely, precisely in a slightly larger form such that the electrode set can, indeed, be comfortably inserted, but that it is well fixed in position therein. Due to the minimum thickness of the employed fleece material, undesired transverse currents between the individual electrode fields are negligibly small.

Naturally, an inventive application apparatus of this type, in addition to being used for electrode systems of stimulation current treatment, can also be employed for electrode systems for tapping bioelectric signals from the patient's body, such as EKG or the like.

It will be apparent that many modifications and variations may be effected without departing from the scope of the novel concepts and teachings of the present invention.

We claim as our invention:

1. Apparatus for application of an electrode configuration to a patient's body; said apparatus comprising an electrode system including a flexible formed part of electrically insulating plastic, individual electrode contact means for transmitting electrical signals secured to said flexible formed part and supported thereby, and a carrier means for a contacting agent for insertion between the electrode contact means and the application location on the patient's body, characterized in that the carrier means for the contacting agent is a fleece material part (2) formed of two superimposed layers each having an exterior contour (8) slightly greater than the exterior perimeter of the formed part (12) of the electrode system (11), the fleece material part (2) having a first side for applying to the patient's body and a second side for contacting the electrode contact means, the fleece material part (2) having a covering (3) of largely impervious insulating material at said second side, said covering (3) having an exterior configuration slightly greater than the exterior perimeter of the formed part (12) of the electrode system and having a first elongated marginal edge portion detached from the fleece material part (2) to define an access opening and having a second elongated marginal edge portion secured with the fleece material part (2) to define a pocket such that the formed part (12) is inserted through the access opening and into a space between the fleece material part (2) and the covering (3), the two superimposed layers of said fleece material part (2) each having a first elongated margin portion extending adjacent but detached from the first elongated marginal edge portion of said covering (3) at said access opening, and each having a second elongated margin portion extending adjacent and secured with the second elongated marginal edge portion of said covering (3), the two superimposed layers of said fleece material part (2) having the respective first elongated margin portions thereof joined by an integral fold connection, and the respective second elongated margin portions being of configurations which are mirror symmetrical in relation to an axis coinciding with the fold connection such that the fleece material part (2) is formed from a flat single layer piece of fleece material having a fold axis and having sections of said fleece material which are mirror symmetrical at the opposite sides of the fold axis.

2. Apparatus according to claim 1, with the two superimposed layers of said fleece material part (2) being made from an irregular fiber fleece material (7) having synthetic wool as a base with polyolefin fibers.

3. Apparatus according to claim 2, with the first and second sides of said fleece material part (2) formed by said two superimposed layers of the irregular fiber fleece material (7) being completely smooth.

4. Apparatus according to claim 1, with the two superimposed layers of said fleece material part (2) and the covering (3) being stitched together at the second elongated margin portions and at the second elongated marginal edge portion to form the pocket for the electrode system (11).

5. Apparatus according to claim 4, with the covering (3) having a recess (4) centrally at said first elongated marginal edge portion thereof.

6. Apparatus according to claim 1, with the covering (3) being formed from a transparent sheet of synthetic plastic insulating material.

7. Apparatus according to claim 6, with said covering (3) being a transparent sheet with polyvinyl chloride as a base.

* * * * *